United States Patent
Bonham et al.

(10) Patent No.: US 10,001,127 B2
(45) Date of Patent: Jun. 19, 2018

(54) PORTABLE DC COOLING FAN WITH SIMULATED OSCILLATION

(71) Applicants: Gary Todd Bonham, Morton, IL (US); Dale Thomas, Cleveland, GA (US)

(72) Inventors: Gary Todd Bonham, Morton, IL (US); Dale Thomas, Cleveland, GA (US)

(*) Notice: Subject to any disclaimer, the term of this patent is extended or adjusted under 35 U.S.C. 154(b) by 629 days.

(21) Appl. No.: 14/286,764

(22) Filed: May 23, 2014

(65) Prior Publication Data
US 2014/0348666 A1    Nov. 27, 2014

Related U.S. Application Data

(60) Provisional application No. 61/826,550, filed on May 23, 2013.

(51) Int. Cl.
*F04D 27/00* (2006.01)
*F04D 25/06* (2006.01)
(Continued)

(52) U.S. Cl.
CPC ........ *F04D 27/004* (2013.01); *A61M 21/02* (2013.01); *F04D 25/0606* (2013.01); (Continued)

(58) Field of Classification Search
CPC .... F04D 27/004; F04D 19/002; F04D 23/006; F04D 25/0606; F04D 25/0693; F04D 25/10; F04D 27/007; F04D 27/008; F04D 27/0223; F04D 29/005; F04D 29/002; F04D 29/522; F04D 29/661; F04D 27/0261; F04D 29/667
See application file for complete search history.

(56) References Cited

U.S. PATENT DOCUMENTS 5,130,587 A * 7/1992 Janisse .................. H02K 11/40
                                                              310/89
5,193,984 A * 3/1993 Lin ......................... F04D 29/64
                                                              362/96
(Continued)

OTHER PUBLICATIONS

Cherry Rocker Switches, Mouser Electronics Catalog 2012, p. 1839.
(Continued)

*Primary Examiner* — Essama Omgba
*Assistant Examiner* — Timothy Solak
(74) *Attorney, Agent, or Firm* — Wendy Thai

(57) ABSTRACT

The invention provides a portable DC cooling fan that performs the dual function of a cooling fan and a sleep aid by generating air movement and white noise useful for inducing sleep. The portable device includes a DC axial fan under the control of an electrical control system that receives power through an AC/DC adapter. The electrical control system includes one or more user interface switches for selecting fan speed and optionally, selecting oscillation mode, thereby simulating the sounds of an oscillating fan without undergoing rotation. The portable DC cooling fan of the invention includes a housing having a plurality of openings on its front and rear surfaces that enable air flow through the device. The invention also provides an article of manufacturer comprising an AC/DC adapter packaged with a portable DC cooling fan of the invention.

20 Claims, 10 Drawing Sheets

(51) Int. Cl.
  *F04D 25/10* (2006.01)
  *F04D 29/00* (2006.01)
  *A61M 21/02* (2006.01)
  *A61M 21/00* (2006.01)
  *F24F 7/007* (2006.01)

(52) U.S. Cl.
  CPC ......... *F04D 25/0693* (2013.01); *F04D 25/10* (2013.01); *F04D 29/005* (2013.01); *A61M 2021/0027* (2013.01); *A61M 2021/0066* (2013.01); *F24F 7/007* (2013.01)

(56) References Cited

U.S. PATENT DOCUMENTS

| | | | | |
|---|---|---|---|---|
| 5,256,039 | A * | 10/1993 | Crawford | F04D 27/00 416/100 |
| 5,468,124 | A * | 11/1995 | Chen | F04D 29/626 415/129 |
| 6,066,211 | A * | 5/2000 | Sandell | A47L 5/24 134/21 |
| 6,222,987 | B1 * | 4/2001 | Duke | A47J 47/14 219/387 |
| 6,454,537 | B1 | 9/2002 | Perella et al. | |
| 6,454,539 | B1 | 9/2002 | Santos | |
| 6,493,243 | B1 * | 12/2002 | Real | H02J 9/062 307/66 |
| 6,590,175 | B1 | 7/2003 | Lam | |
| D529,166 | S | 9/2006 | Geringer | |
| D572,359 | S | 7/2008 | Zhuang | |
| 2005/0036286 | A1 * | 2/2005 | Kuan | G06F 1/181 361/679.33 |
| 2007/0069471 | A1 * | 3/2007 | Brattesani | A63F 9/0079 273/317 |
| 2010/0143125 | A1 * | 6/2010 | Vogel | F04D 27/006 416/61 |
| 2011/0026220 | A1 * | 2/2011 | Tai | G06F 1/206 361/679.48 |
| 2011/0198995 | A1 * | 8/2011 | Salter | B60H 1/00985 315/51 |
| 2011/0216007 | A1 * | 9/2011 | Cheng | G06F 3/02 345/168 |
| 2011/0262271 | A1 | 10/2011 | Fukuda et al. | |
| 2012/0087812 | A1 | 4/2012 | Greenberg | |

OTHER PUBLICATIONS

Gerald Tan, Fundamentals of Brushless DC Axial Cooling Fans, Sanyo Denki America, Inc., Mar. 31, 2008.
NMB Minebea, Axial Cooling Fans, available at http://www.nmbtc.com/fans/axialcooling.html, last retrieved May 8, 2013.
NMB Minebea, Axial DC Cooling Fan in Computers, available at http://www.nmbtc.com/dc-fans/axialdccooling.html, last retrieved May 8, 2013.
NMB Minebea, Axial Fans—Keep Systems' Thermal Problems at Bay, available at http://www.nmbtc.com/fans/axial.html, last retrieved May 8, 2013.
NMB Minebea, Cooling Fan Noise—Why It's Necessary, available at http://www.nmbtc.com/fans/cooling-fan-noise.html, last retrieved May 8, 2013.
NMB Minebea, DC Axial Fans, available at http://www.nmbtc.com/dc-fans/, last retrieved May 8, 2013.
NMB Minebea, Electrical Differences in AC and DC Cooling Fans, available at http://www.nmbtc.com/ac-fans/acdccooling.html, last retrieved May 8, 2013.
NMB Minebea, What is a DC Cooling Fan, available at http://www.nmbtc.com/dc-fans/dccoolingwhatis.html, last retrieved May 8, 2013.
Sanyo Denki DC Fans, Mouser Electronics Catalog 2012, p. 3011 & 3013.

* cited by examiner

PORTABLE DC COOLING FAN WITH SIMULATED OSCILLATION

CROSS-REFERENCE TO RELATED APPLICATIONS

This application claims priority to U.S. provisional applications 61/826,550, filed May 23, 2013, the contents of which are incorporated herein by reference in its entirety.

BACKGROUND

Significant energy consumption in homes and commercial buildings can be attributed heating, ventilation and air conditioning. Electrical fans consume significantly less energy than air conditioning, and thus provide a means to reduce energy costs associated with achieving comfortable living spaces. For example, electrical fans can be used to improve circulation, for cooling particularly at temperatures below 80°, or to cool a selected space or an individual rather than an entire room or entire house. Thus, the strategic use of an electrical fan can lessen air conditioning use and reduce energy consumption.

SUMMARY OF THE INVENTION

The invention provides a small, portable DC cooling fan that performs the dual function of a cooling fan and a sleep aid by generating air movement and white noise useful for inducing sleep.

In one aspect, the invention provides a portable DC cooling fan having: (a) a DC axial fan electrically connected to an electrical control system to enabling the electrical control system to control operation of the fan, the electrical control system being electrically connected to a DC power jack and having at least one user interface switch through which a user can control operation of the DC axial fan; and (b) housing within which the DC axial fan is secured having an opening through which the DC power jack is mounted, an opening for accommodating the user interface switch to enable access to the switch from the exterior of the housing, and a plurality of regularly-spaced openings substantially aligned with the blades of the axial fan to enable efficient air intake and egress through the housing.

In some embodiments of a portable DC cooling fan of the invention, the user interface switch is a rocker switch having three contacts that enable the user to power off the fan or select between one of two fan speeds when powering on the fan. In some embodiments, the user interface switch is a tactile switch.

In some embodiments of a portable DC cooling fan of the invention, the electrical control system includes three tactile user interface switches, a fan micro-controller for monitoring the actuation of the tactile switches, and a buck regulator through which the fan micro-controller adjusts the DC voltage being provided to the fan, and wherein: (a) each of the tactile switch is accessible from the exterior of the housing through an opening in the housing configured to accommodate the tactile switch thereby enabling the user to actuate the switch from the exterior of the housing; and (b) each of the tactile switch is electrically connected to the fan micro-controller, which is electrically connected to a buck regulator configured to provide operating voltage to the fan to allow the user to control fan operation by actuating one or more tactile switches.

In some embodiments, actuation of (a) a first tactile switch causes the micro-controller to turn the fan on or off, (b) a second tactile switch configured for fan speed selection causes the micro-controller to alter the speed of the DC axial fan, and (c) of a third tactile switch configured for oscillation mode selection causes the micro-controller to turn on or off fan speed oscillation.

In some embodiments, actuation of the tactile switch for fan speed selection causes a change in the DC voltage being provided to the fan motor thereby enabling the user to affect fan speed. In some embodiments, each actuation of the tactile switch for fan speed selection causes fan speed to increase to the next higher speed increment, and actuation of the tactile switch for fan speed selection when the fan is operating at the highest possible speed causes fan speed to return to the lowest speed.

In some embodiments, selection of the oscillation mode causes the portable DC cooling fan to continuously cycle through four fan operation phases: (a) a first phase during which the fan is maintained at a pre-selected speed for a first length of time, (b) a second phase during which fan speed decreases from the pre-selected speed to the lowest setting over a second length of time, (c) a third phase during which fan speed is maintained at the lowest fan speed for a third length of time, and (d) a fourth phase during which fan speed increases from the lowest fan speed to the pre-selected speed over a fourth length of time. In some embodiments, the first and third periods are about 2 to about 3 seconds. In some embodiments, the second and fourth periods are about 5 to about 6 seconds.

In some embodiments, the buck regulator is configured to provide an operating voltage of about 6 volts, about 8 volts, about 10 volts, about 12 volts, or any combination thereof to the motor of the DC axial fan.

In some embodiments, a portable DC cooling fan of the invention further includes a membrane overlay with demarcation indicating the position of a tactile switch, notation indicating the function of a tactile switch when actuated, or both, thereby forming pushbuttons through which a user can operate the portable DC cooling fan.

In some embodiments, the portable DC cooling fan further includes an LED light source for illuminating the pushbutton, the LED being under the control of the fan micro-controller.

In some embodiments, the fan is powered using a current of about 1 ampere or less. In some embodiments, the electrical control system operates from a 12 volt, 1 ampere AC/DC adapter power supply. In some embodiments, the DC axial fan has an air output at about 12 to about 200 cubic feet per minute.

In another aspect, the invention provides an article that includes a portable DC cooling fan of the invention, an AC/DC adapter and packaging material. In some embodiments, the AC/DC power adapter is a 12-volt, 1-ampere AC/DC adapter.

In one aspect, the invention provides a portable DC cooling fan having the dual-function of a cooling fan and a white noise generator. The portable fan includes an electrical assembly disposed in a housing, the electrical assembly having a DC axial fan electrically connected to a DC power jack and an electrical switch, thereby allowing the electrical switch to direct current from the DC power jack to the fan, the DC power jack and electrical switch being functionally accessible from the exterior of the housing; and the housing having a plurality of openings on its front and rear panels that enable maximum air flow through the device.

In some embodiments, the DC axial fan has a brushless DC motor. In some embodiments, the DC power jack is effective to receive power from an AC power supply of about 120 V. In some embodiments, the electrical switch is a rocker switch. In some embodiments, the electrical switch has at least three contacts. In some embodiments, two of the contacts are connectable to the brushless DC motor. In some embodiments, one of the two contacts connectable to the brushless DC motor is connectable to the brushless DC motor through a resistor. In some embodiments, the resistor is a surface mounted device. In some embodiments, the resistor has a resistance of about 5 Ohm. In some embodiments, the resistor has a voltage of about 10 W. In some embodiments, the resistor has a resistance of about 5 ohms and a voltage of about 10 W. In some embodiments, the fan is powered at a voltage of about 5, about 12, about 24, or about 48 volts DC. In some embodiments, the fan is powered using a current of about 1 ampere or less.

In some embodiments, the housing is box-shaped. In some embodiments, the box-shaped housing is less than about 10 inches tall, less than about 10 inches wide, or less than about 10 inches tall and less than about 10 inches wide. In some embodiments, the height of the device housing is about three or more times the depth of the device housing. In some embodiments, the height and width of the device are about 5 inches, and the depth of the device is about 1 and ¾ inches. In some embodiments, the weight of the device is about 1 pound or less than about 1 pound.

In some embodiments, the plurality of openings on the housing forms a grill pattern coextensive with the circular path of the fan blades. In some embodiments, the grill pattern has an inner peripheral edge that substantially aligns with the hub of the DC axial fan. In some embodiments, the grill pattern has an outer peripheral edge that substantially aligns with the circular path traced by the trailing edge of the blades. In some embodiments, the grill pattern has an inner peripheral edge that substantially aligns with the hub of the DC axial fan and an outer peripheral edge that substantially aligns with the circular path traced by the trailing edge of the blades. In some embodiments, the grill pattern has a plurality of curved openings. In some embodiments, the width of the openings is narrower than the width of a finger.

In some embodiments, the device produces a sound output from about 1 decibel to about 60 decibels. In some embodiments, the device produces a sound output at about 10 to about 40 decibels. In some embodiments, the device has air output at about 12 to about 200 cubic feet per minute.

In another aspect, the invention provides an article of manufacture that includes a portable device of the invention and an AC/DC adapter effective transmit power to the device through the DC power jack.

Any feature or combination of features described herein are included within the scope of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION OF THE INVENTION

Figure 1A:
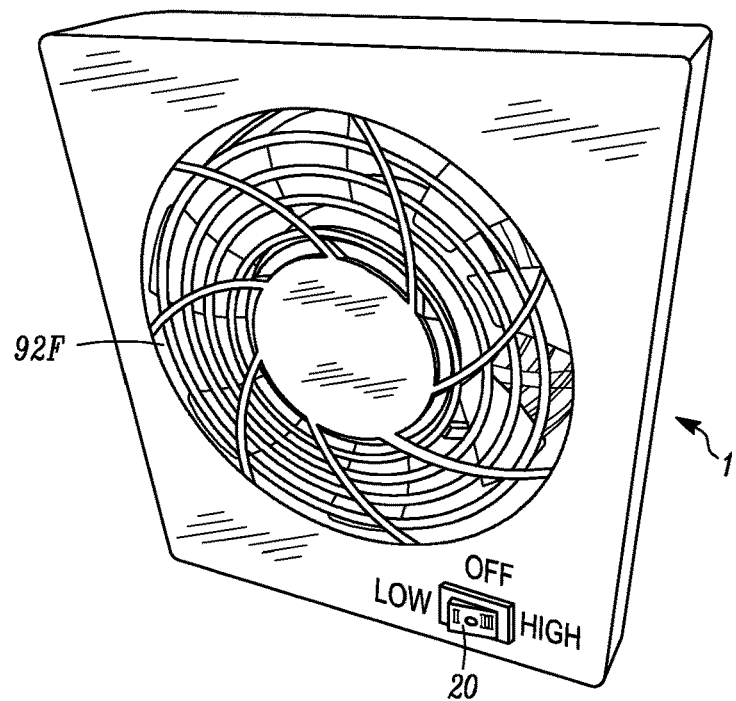
FIGS. 1A, 1B and 1C are perspective views of a dual-function, portable fan with rocker switch including a front perspective view (1A), a rear perspective view (1B), and a rear perspective view of the portable fan in which an AC/DC power adapter is inserted into a DC power jack on the rear of the fan (1C).

The invention provides a small, portable DC cooling fan that performs the dual function of a cooling fan and a sleep aid by generating air movement and white noise useful for inducing sleep. A portable DC cooling fan of the invention includes a DC axial fan electrically connected to a control system that operates from an AC/DC adapter power supply. The electrical control system includes a user interface switch for receiving input from the user and through which the user can control operation of the DC axial fan.

DC Axial Fan

As used herein, the term "DC axial fan" refers to a fan having a motor that operates on direct current (DC) electricity to drive the fan blades to move air in a direction substantially along the axis of the fan or in a direction substantially parallel to the shaft about which the blades rotate. DC axial fans are known to those of skill in the art, e.g., see http://www.nmbtc.com/do-fans/ (last visited May 20, 2013); G. Tan, *Fundamentals of Brushless DC Axial Cooling Fans*, available at http://www.newark.com/pdfs/techarticles/sanyo/fundamentals_brushlessDCcooling-Fans.pdf (last retrieved May 20, 2013); and http://en.wikipedia.org/wiki/Brushless_DC_electric_motor (last visited May 20, 2013). DC axial fans can be purchased from a variety of sources including, for example, www.ebmpapst.us and http://www.pelonistechnologies.com. See also http://www.ebmpapst.us/media/content/products/downloads/DC_axial_fans_2011.pdf (retrieved May 22, 2014). The following table provides specifications for two DC axial fans from that can be used in a portable DC cooling fan of the invention. Fan 1 (Model RD12038S12H) and Fan 2 (Model RSH1238B12N32PA) have auto start feature, and Fan 2 has a speed control mode utilizing pulse width modulation (PWM).

|  | FAN 1 | FAN 2 |
|---|---|---|
| General Specification | | |
| Dimensions | 120 × 120 × 38 mm | 120 × 120 × 38 mm |
| Bearing type | Long Life Sleeve Bearing | Two Ball Bearing |
| Rated Voltage | 12 V DC | 12 V DC |
| Operating Voltage | 7.5 V to about 13.5 V | 6 V to about 14 V |
| Start-up Voltage | ≤7.5 V | ≤6 V |
| Rated Current | ≤0.55 A + 10% | ≤0.62 A + 10% |
| Rated Power | ≤6.6 W + 10% | ≤7.44 W + 10% |
| Rated Speed | 3200 RPM/min ± 10% | 3200 RPM/min ± 10% |
| Max. Air Flow | 132 CFM (224.14 m$^3$/h) | 132.8 CFM (225.5 m$^3$/h) |
| Max. Static Pressure | 12.1 mm-H$_2$O (0.48 in.-H$_2$O) | 12.1 mm-H$_2$O (0.48 in.-H$_2$O) |
| Noise Level | 42 dBA at rated voltage, distance of about 1 meter in mute room (background noise <18 dB) | 45.8 dBA at rated voltage, distance of about 1 meter in mute room (background noise <18 dB) |
| Life Expectance | 30,000 hours at 40° C. | 50,000 hours at 40° C. |
| Pole | 4 poles | 4 poles |
| Electrical Specification | | |
| Locked Rotor Protection | Auto powers off after locked at rated voltage for 1 seconds, and then circuit attempts to resart in 2-6 seconds | Auto powers off after locked at rated voltage for 1 seconds, and then circuit attempts to resart in 2-6 seconds |
| Polarity Protection | Open circuit when Vcc & GND are exchanged | Open circuit when Vcc & GND are exchanged |
| Insulation Resistance | At least 10 MΩ at 500 VDC between housing and both lead wires | At least 10 MΩ at 500 VDC between housing and both lead wires |
| Dielectric Strength | Withstand 500 VAC for 1 minute 1 mA betwteen housing and both lead wires | Withstand 500 VAC for 1 minute 1 mA betwteen housing and both lead wires |
| Main Material | | |
| Frame | Polybutylene terephthalate | Polybutylene terephthalate |
| Propeller | Polybutylene terephthalate | Polybutylene terephthalate |
| Bobbin | Polybutylene terephthalate | Polybutylene terephthalate |
| Lead wires | RED (+), black (−), UL1007#22AWG, 250 mm ± 5 mm | RED (+), black (−), UL1007#24AWG, 310 mm ± 5 mm |
| Environment Specification | | |
| Operating Temperature | About −10° C. to about +70° C. | About −10° C. to about +70° C. |
| Operating Humidity | About 15% to about 90% RH | About 15% to about 90% RH |
| Storage Temperature | About −20° C. to about +85° C. | About −20° C. to about +85° C. |
| Storage Humidity Range | About 15% to about 90% RH | About 15% to about 90% RH |

The DC axial fan can be powered using an external power supply, for example, using an AC/DC (alternating current/direct current) power adapter. AC/DC power adapters are well known to those of skill in the art. A non-limiting example of an AC/DC power adapter is a 12 Volt, 1 Amp AC/DC power adaptor. The AC/DC power adapter supplies power to the DC axial fan through a DC power jack such as, for example, a 12 Volt power jack, a portion of which is accessible from the exterior of the housing and to which the DC connector portion of the AC/DC power adaptor can be inserted.

Operation of the DC axial fan can be controlled by an electrical control system that receives input power from the AC/DC adapter and supplies appropriate operating voltages to the fan. The electrical control system can include one or more user interface switches, e.g. one, two, three or four, for example, that are electrically connected with one or more components that provide appropriate operating voltages based on user actuation of the switches. The user interface switch can be a rocker switch or a tactile switch. The electrical control system can include a controller such as a micro-controller to which the user interface switches can be electrically connected to enable the controller to monitor actuation of the user interface switches. The electrical control system can include a buck regulator to which the fan is electrically connected and with which the micro-controller can operate to provide the appropriate operating voltage to the fan. The electrical control system can include an LED driver to control illumination of one or more LED light source and allow illumination of select operator control components when actuated. The electrical control system can be a printed circuit board (PCB) to which the switches can be soldered and to which the micro-controller and components making up the LED driver, buck regulator can be incorporated as known to those of skilled in the art.

Operator control component can be a control panel with pushbuttons formed by appropriate demarcations and/or notations on a membrane overlay. The demarcations and/or notations can align with the position of one or more user interface switches thereby forming pushbuttons that allow the user to control fan operation or activate one or more features.

A portable DC cooling fan of the invention can have a speed control feature allowing the user to select from two or more speeds. For example, the speed control feature can allow the user to select a high or low speed. Alternately, the speed control feature can allow the user to select among four different fan speeds, for example, a low, low-medium, medium or high speed.

A portable DC cooling fan of the invention can have an oscillation mode feature that allows the user to turn on or off a speed oscillation feature that mimics a standard oscillating fan without rotating from side to side. In contrast to a standard oscillating fan, which rotates from side to side blowing air in different direction as it rotates, the simulated oscillation or speed oscillation mode of a portable DC cooling fan of the invention blows air in one direction. A fan of the invention simulates a standard oscillation fan by cycling between periods of maximum and minimum speed with periods of decreasing or increasing speeds therebetween by maintaining a pre-selected, maximum fan speed, maintaining the minimum available fan speed, with intervals of increasing or decreasing speeds therebetween.

As such, when fan speed decreases, air and sound output from the non-rotating portable DC cooling fan decreases simulating the effect of a standard oscillating fan that is rotating away from an observer. As fan speed is maintained at the minimum available speed, the air and sound output from the portable DC cooling fan is at a minimum level simulating the effect of a standard oscillating fan that is rotated the greatest distance away from the observer. In contrast, as fan speed increases, air and sound output from the portable DC cooling fan increases simulating the effect of a standard oscillating fan that is rotating toward the observer, and as fan speed is maintained at the pre-selected, maximum speed, air and sound output from the portable DC cooling fan is at its greatest level simulating the effect of a standard oscillating fan that is directed at the observer. Thus, through speed oscillation achieved by cycling through phases of constant speed (maximum or minimum) with phases of increasing and decreasing speeds therebetween, a non-rotating, portable DC cooling fan of the invention which blows air in one direction can simulate a standard oscillating fan which blows air in more than one direction through fan rotation.

Thus, the control panel of a fan of the invention can include: (1) an On/Off pushbutton for setting the fan to an on or off position; (2) a Speed Control pushbutton, which can be used to select one of four fan speeds: low, low-medium, medium and high; as well as a Oscillation mode pushbutton, for use in turning the oscillation mode on or off. When oscillation mode is selected or turned on, the fan continuously cycles between two speeds, a maximum speed and the lowest fan speed. The maximum speed is a preselected fan speed, which can be low-medium, medium or high. Each oscillation cycle includes four phases: (1) a first phase during which the fan is maintained at the maximum speed, i.e. pre-selected speed, for a first select period of time, (2) a second phase during which fan speed decreases to the lowest setting, e.g. low speed over a second selected period of time, (3) a third phase during which the fan is maintained at the lowest speed for a third selected period of time, and (4) a fourth phase during which fan speed increases to the maximum speed, i.e. a pre-selected speed, over a fourth selected period of time. Each phase of an oscillation cycle or each period can be any length of time including, without limitation, 2, 3, 4, 5, 6, 7, 8, 9, 10 or more than 10 seconds. An oscillation cycle can include phases having any combination of time interval. For example, when oscillation mode of portable fan 101 is selected, the fan continuously cycles between a preselected speed and the lowest fan speed as follows: fan speed is maintained at the pre-selected speed for 2 seconds, fan speed decreases to the lowest speed in the next 5 to 6 seconds; fan speed is maintained at the lowest speed for 2 seconds, fan speed increases to the pre-selected speed within the following 5 to 6 seconds. Thus, when oscillation mode is selected, the fan continuously cycles between a pre-selected speed and the lowest fan speed, each cycle occurring over, for example and without limitation, 10, 12, 14, 16, 18, 20, 22, 24, 26, 28, 30 or more than 30 seconds.

Components of a portable fan of the invention including axial fan and motor, membrane graphic overlays, power supply, power jack, wires, plug ins or other electronic components making up the PCB can be purchased from any electronic supply company including, for example, Mouser Electronics (www.mouser.com) Digi-key (www.digikey.com) Data Graphics (www.datagraphics.com).

The DC axial fan, electronic control system, as well as a portion of the DC power jack are enclosed by and secured within a housing that includes an opening through which the DC power jack is mounted, an opening through which a user interface switch can be accessed from the exterior of the housing, and a plurality of regularly-spaced openings on portions of the housing that flank the DC axial fan—the plurality of regularly-spaced openings forming g grill pattern having an inner circular edge that aligns with the circumference of the hub of the DC axial fan and an outer circular edge aligns with the path of the edge of the fan blade so as to allow for efficient air intake into the housing and efficient air egress from the housing.

The housing of the portable DC cooling fan of the invention can be of any shape including box-type and can be made of any materials such as metal or plastic including one or more synthetic or nonsynthetic materials. The housing can be produced using any method known to those of skilled in the art including, for example, by injection molding using a variety of materials known to those of skill in the art. The housing can be formed using by injection molding using materials known to those of skill in the art. Examples include, without limitation, thermoplastics such as polyester resin, acetal resin, nylon resin and other engineering-type thermoplastics such as acetals. Additional examples include: ultra-high-molecular-weight polyethylene (UHMWPE), Nylon 6, Nylon 6-6, polytetrafluoroethylene (PTFE/Teflon), acrylonitrile butadiene styrene (ABS), polycarbonates (PC), polyamides (PA), polybutylene terephthalate (PBT), polyethylene terephthalate (PET), polyphenylene oxide (PPO), polysulphone (PSU), polyetherketone (PEK), polyetheretherketone (PEEK), polyimides, polyphenylene sulfide (PPS), polyoxymethylene plastic (POM/Acetal), high-density polyethylene, polyvinyl chloride, low-density polyethylene, polypropylene, polyamides, acrylonitrile butadiene styrene, polycarbonate/acrylonitrile butadiene styrene, and polyetheretherketone.

The dual function portable DC cooling fan of the invention, which functions as a cooling fan and a white noise generator, can be used as a portable fan for cooling and improved circulation, as well as a source of white noise that can be used to facilitate sleep. The DC axial fan can have an air output range between about 12 and greater than 200 cubic feet per minute (about 1800 to about 5000 RPM), and a noise output from about 1 decibel to about 70 decibels. As such, the device can be used in a variety of settings or circumstances in which a lower or higher air and/or sound output is desired. For example, the device can be used in an office where low noise may be desirable or in a bedroom where white noise can facilitate sleep. The grill pattern includes openings of a size sufficient to allow maximum airflow while maintaining safety, e.g. preventing contact of limbs and fingers with the fan blades.

The portable DC cooling fan of the invention has a small footprint, for example, less than a foot wide, a foot high and 3 inches thick, and is lightweight, for example can be less than about 2 pounds in weight. The portable DC fan of the invention can have dimensions of about 5¼ inches wide, about 6¼ inches high and about 1¾ inch deep, and can be less than about 1 pound in weight. As the device operates at low voltages and current, for example, at about 5, 12, 24 or 48 V DC and about 1 ampere or less, the device has a reduced fire risk, enhanced safety and less need for use with a ground fault circuit interrupter (GFCI) receptacle. The device can have a life of about 50,000 hours of continuous use and is particularly useful as a travel fan due to its small size, lightweight and usability with a 120 Volt AC power source. As the device has enhanced safety, produces white noise and can generate a high volume of air in relation to its size, the device can be used as a portable sleep fan.

EXAMPLES

Example 1—Portable DC Cooling Fan with Speed Selection

Figure 1B:
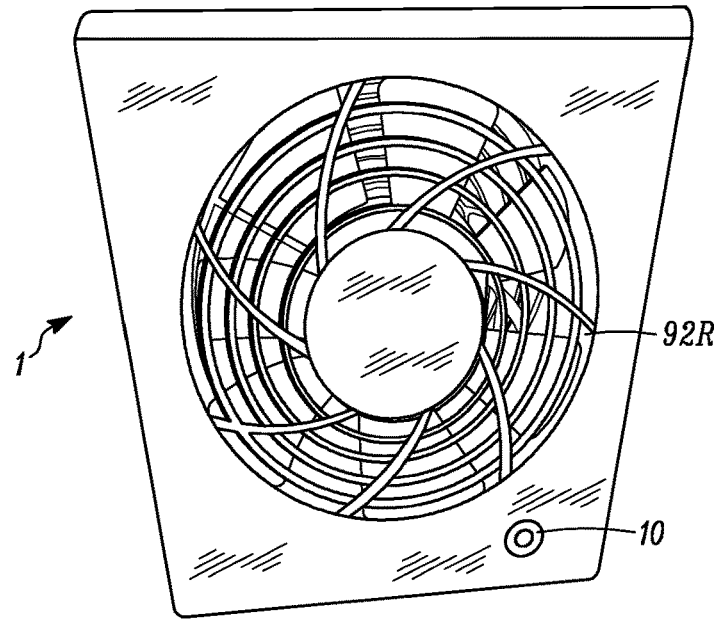
Figure 1C:
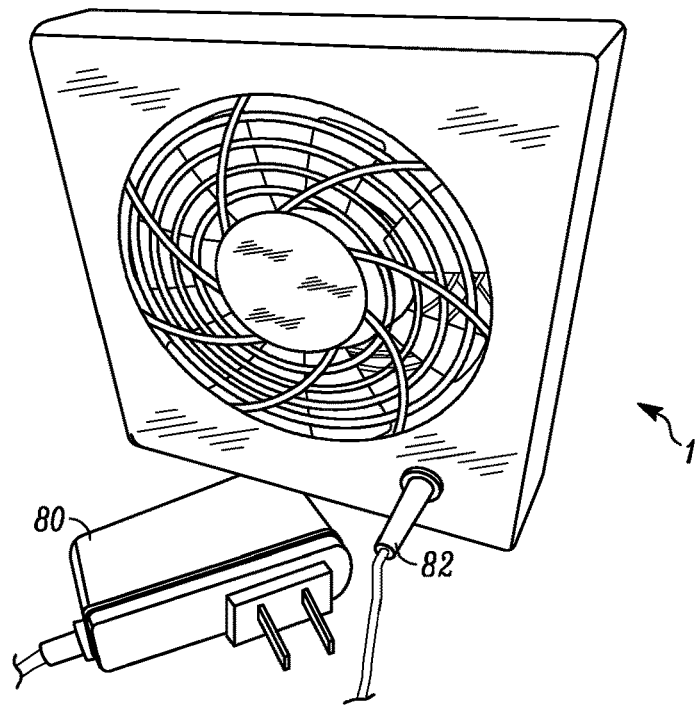

An embodiment of a portable fan of the invention is illustrated in FIGS. 1A-1C. FIGS. 1A and 1B provide a front and rear perspective view, respectively, of dual function, portable fan 1. Portable fan 1 has Low-Off-High rocker switch 20 disposed at the front of fan 1 and is accessible from the exterior of the housing. Portable fan 1 can be set at a low or high speed using rocker switch 20. See FIG. 1A. Power to portable fan 1 is provided through metal, panel-mount DC power jack 10, which is disposed at the rear of fan 1. See FIG. 1B. Power can be supplied to portable fan 1 through DC power jack 10 using an AC/DC power adapter. See FIG. 1C.

Figure 2A:
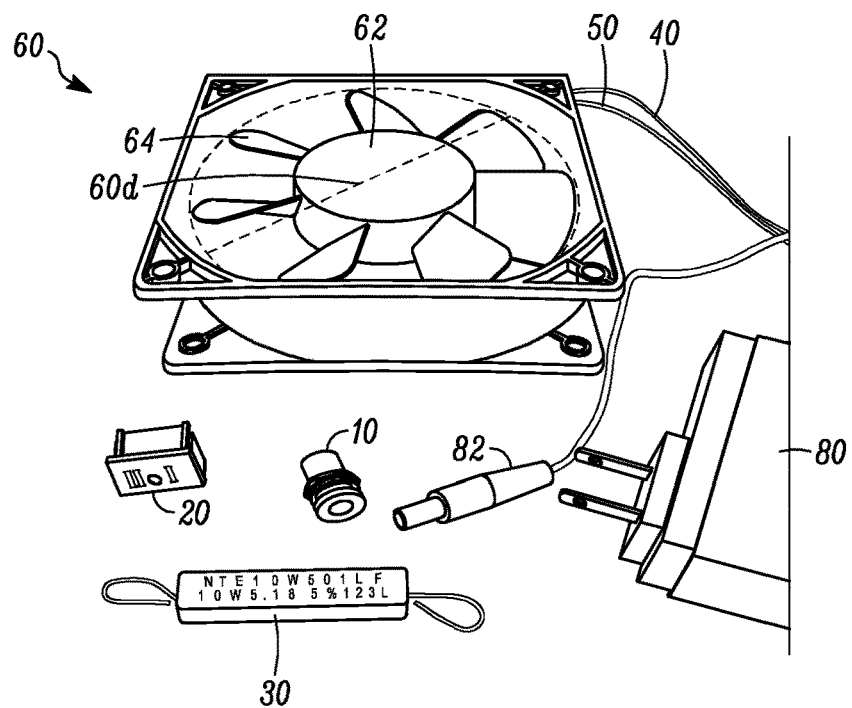
FIGS. 2A and 2B illustrate components of the dual-function portable fan (2A) in the electrical circuit (2B).

Electrical components of portable fan 1 are provided in FIG. 2A. These include DC axial fan 60 with leads 40 and 50, metal panel mount DC power jack 10, rocker switch 20 and resistor 30. DC axial fan 60 has 7 of blade 64 attached to hub 62 with hub diameter 62d, the blades and hub forming a wheel diameter represented by line 60d. Axial fan 60 includes frame 68 and a motor (not shown) that operates on DC electrical power. DC axial fan 60 is electrically connected to rocker switch 30 and DC power jack 10 through leads 40 and 50, thereby enabling rocker switch 30 to control the flow of electricity from power jack 10 to axial fan 60 and thus allowing electricity supplied to power jack 10 to power axial fan 60. Electrical power to portable fan 1 through power jack 10 is supplied using AC/DC power adapter 80 (with DC connector 82).

Figure 2B:
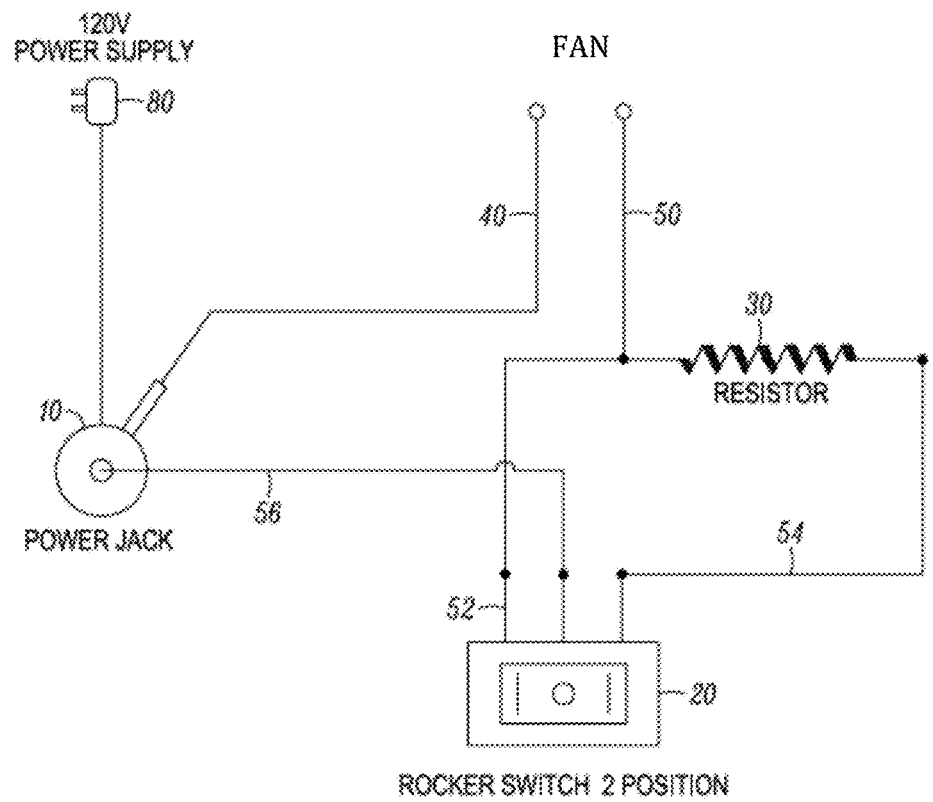

FIG. 2B illustrates the circuitry of portable fan 1. DC power jack 10 supplies electrical power to the DC axial fan through lead 56, which electrically connects power jack 10 to rocker switch 20. When rocker switch 20 is in the off position (O), no electrical power is supplied to the DC axial fan. When rocker switch 20 is set to the high position (II), electrical power is supplied to the DC axial fan through lead 52 and fan input lead 50, which enables the fan to operate at full power. When rocker switch 20 is set to the low position (I), electrical power is supplied to the DC axial fan through lead 54, resistor 30 and fan input lead 50. Resistor 30, connected in series with the DC axial fan, reduces the current supplied to the fan, for example, by half, resulting in the fan functioning at a lower speed relative to that in the absence of resistor 30. Thus, fan speed can be adjusted by placing different resistors in series with the fan. Lead 40 completes the circuit by electrically connecting the DC axial fan to power jack 10.

Figure 3A:
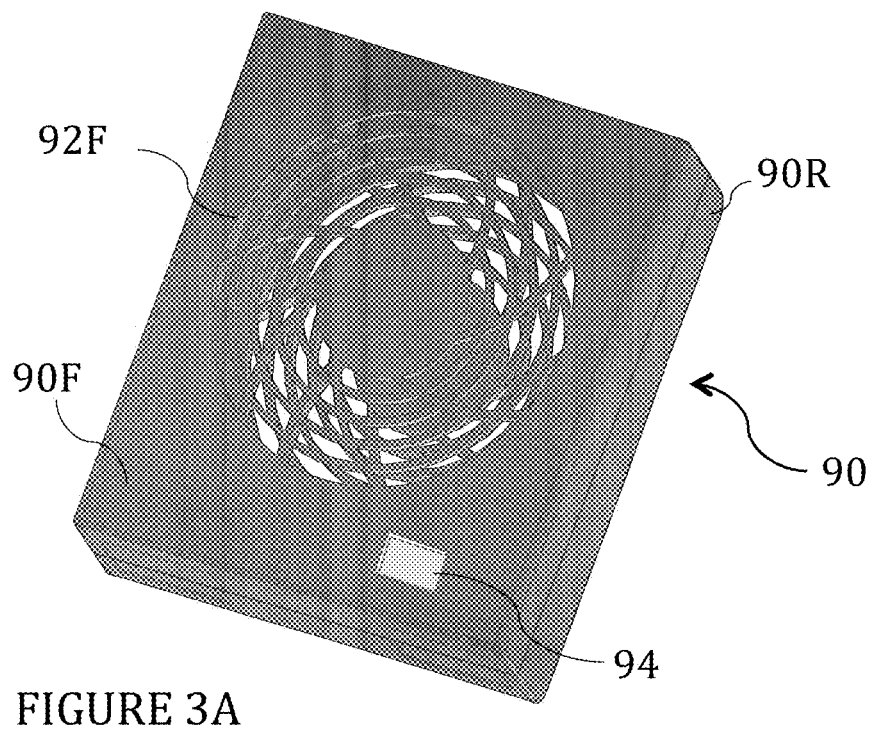
FIGS. 3A-3B are perspective views of a housing of a fan of the invention including a front (4A) and a rear (4B) perspective view.
Figure 3B:
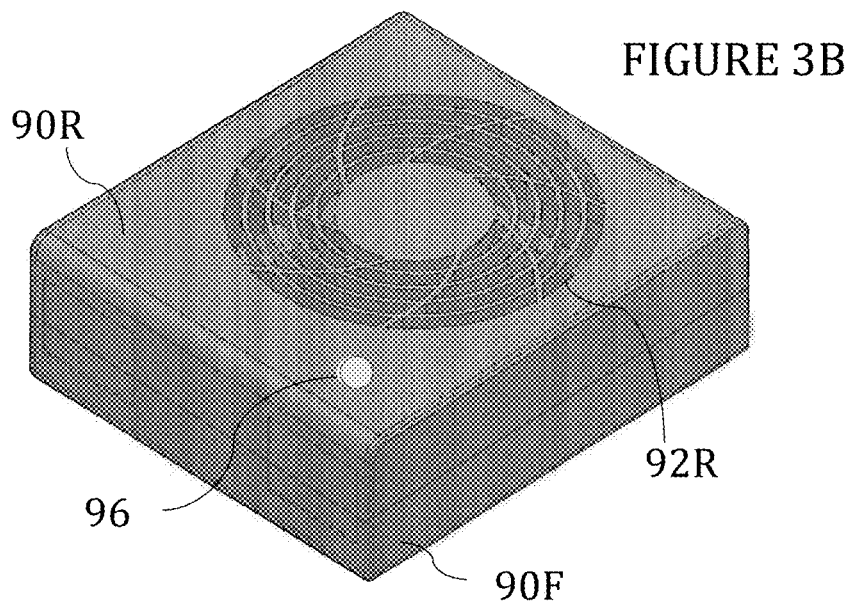
Figure 4A:
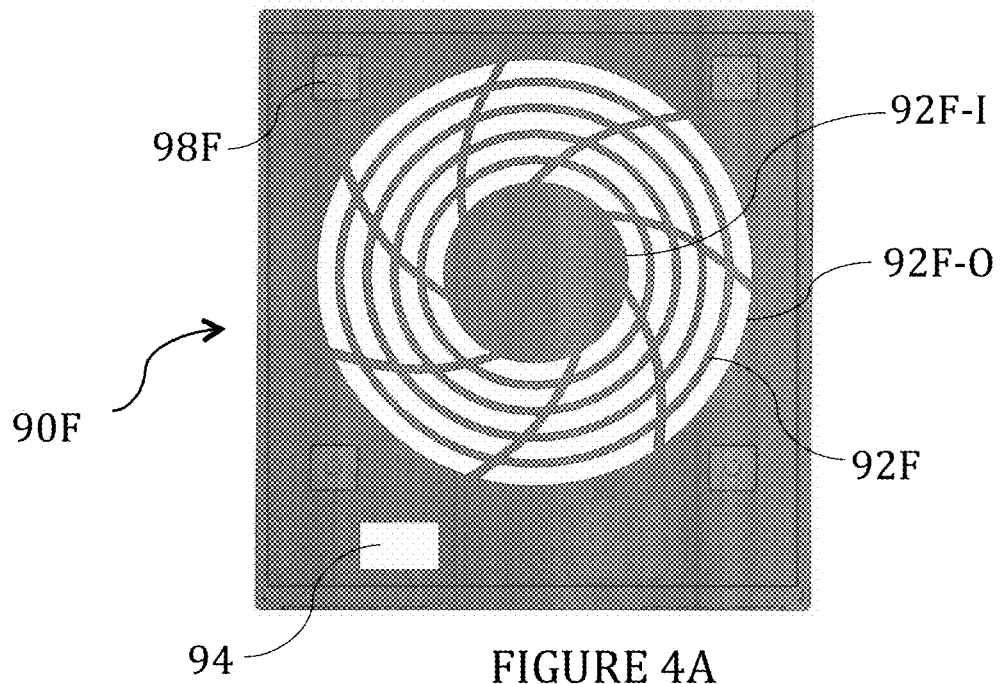
FIGS. 4A-4B are plan views of the interior of a front cover (4A) and a rear cover (4B) of a housing of the invention
Figure 4B:
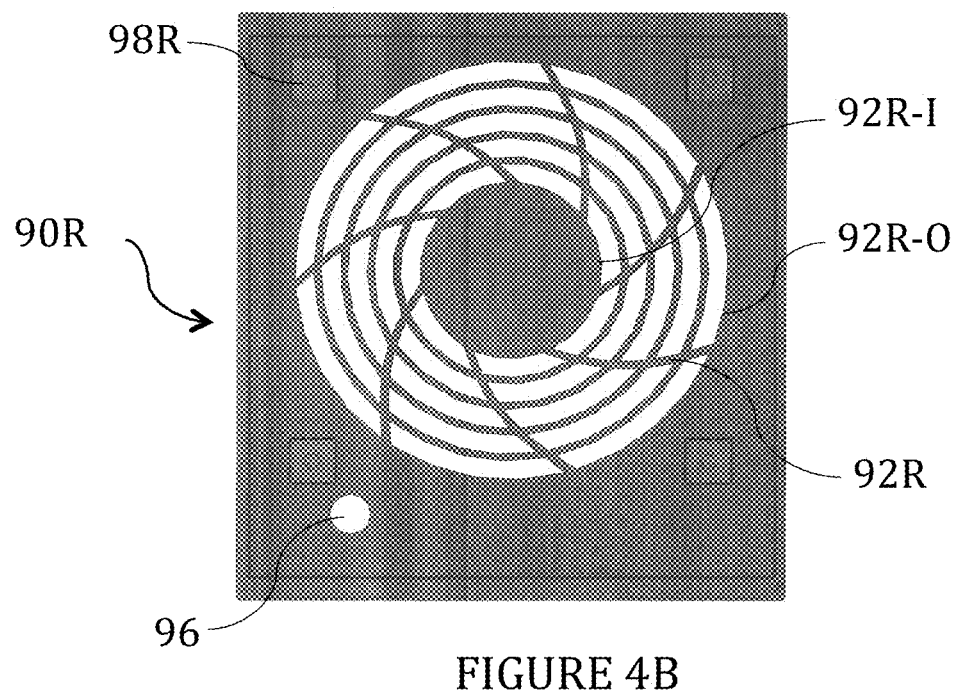

The housing of portable fan 1 is illustrated in FIGS. 3A-3B. A front perspective view of the exterior is provided in FIG. 3A, and a rear perspective view is provided in FIG. 3B. Housing 90 includes a front portion and a rear portion. Plan views of the interior of front portion 90F and rear portion 90R are provided in FIGS. 4A and 4B, respectively. Slot 94 (FIGS. 3A and 4A) on face of front portion 90F is configured to accommodate rocker switch 20, while slot 96 on the face of rear portion 90R (FIGS. 3B and 4B) is configured to accommodate panel-mount DC power jack 10. The face of portion 90F also includes a plurality of regularly spaced openings 92F that radiate from a center hub to form a grill pattern having (1) inner circular edge 92F-I that substantially aligns with the circumference of hub 62 of axial fan 60 (i.e. having a diameter substantially similar to the fan hub diameter); and (2) outer circular edge 92F-O that substantially aligns with a path circumscribed by tip 66 of fan blade 64, which is represented by the dashed curve in FIG. 2A (i.e. having a diameter substantially similar to the fan wheel diameter 60d). Similarly, the face of rear portion 90R of housing 90 includes a plurality of regularly spaced openings 92R that radiate from a center hub to form a grill pattern having (1) inner circular edge 92R-I that substantially aligns with the circumference of hub 62 of axial fan 60 and (2) outer circular edge 92R-O that substantially aligns with a path circumscribed by tip 66 of fan blade 64 (see dashed curve in FIG. 2A). As such, the housing allows for efficient air intake and egress, for example, efficient airflow from the rear to the front of fan 1.

Attachment means 98F and 98R allow DC axial fan 60 to be secured within housing 90 between front portion 90F and rear portion 90R. Attachment means 98F and 98R can be any fastening means known to those of skill in the art including, for example and without limitation, screws or snapfits components.

Figure 5A:
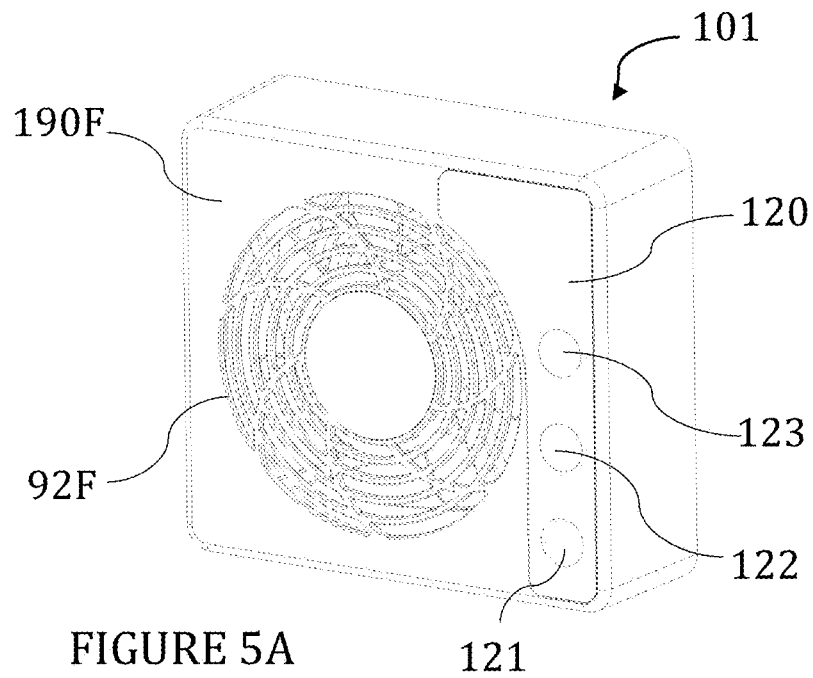
FIGS. 5A-5B are perspective views from the front (5A) and rear (5B) of a dual-function, portable fan having a three-button overlay.
Figure 5B:
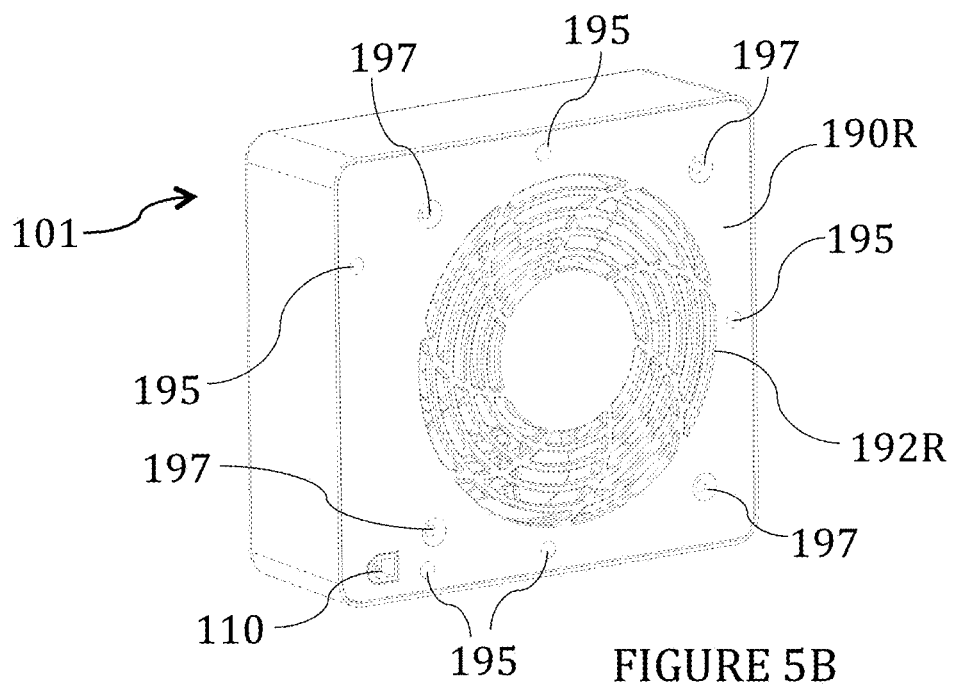

Example 2—Portable DC Cooling Fan with Speed Selection and Simulated Oscillation Another embodiment of a portable fan of the invention is illustrated in FIGS. 5A-5B and 6-8. FIGS. 5A and 5B provide a front and rear perspective view, respectively, of dual function, portable fan 101.

Portable fan 101 has a three-button control panel 120 with pushbutton 120-1, pushbutton 120-2 and pushbutton 120-3 disposed at the front of fan 101 that can be used to turn the fan on or off, as well as select fan speed or oscillation mode. Thus, the three-button control panel 120 includes an on/off button, a speed selection button and an oscillation button. Power to portable fan 101 is provided through metal, panel-mount DC power jack 110 at the rear of fan 101. See FIG. 5B. Similar to portable fan 1, power can be supplied to portable fan 101 through DC power jack 110 using an AC/DC power adapter. The rear and front portion of the housing of portable fan 101 are secured one to the other at five positions through opening 195. The DC axial fan is secured without the housing of portable fan 101 at four positions through opening 197.

Figure 6:
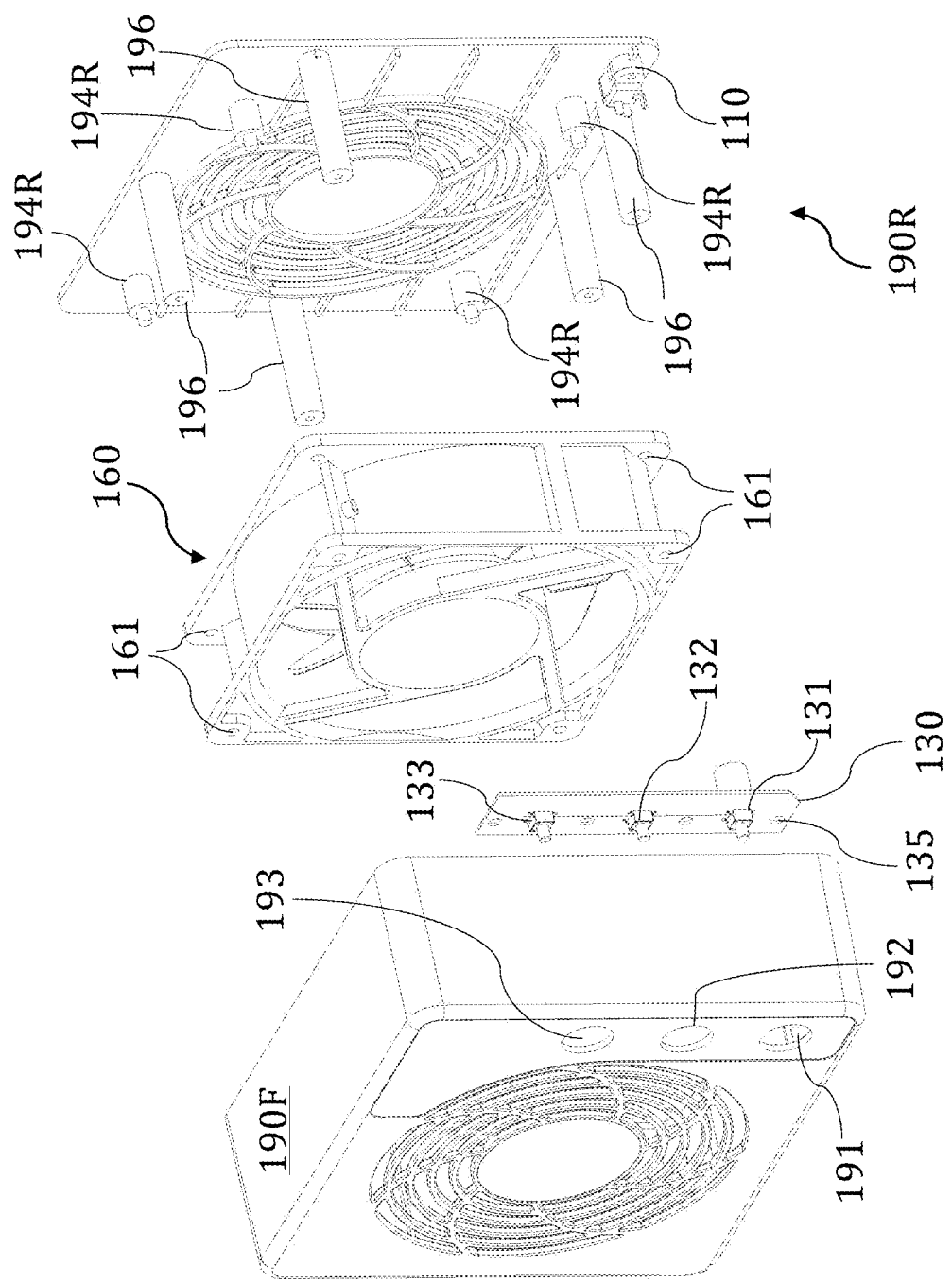
FIG. 6 is an exploded, front perspective view of a dual function, portable fan with a three-button overlay.
Figure 6:
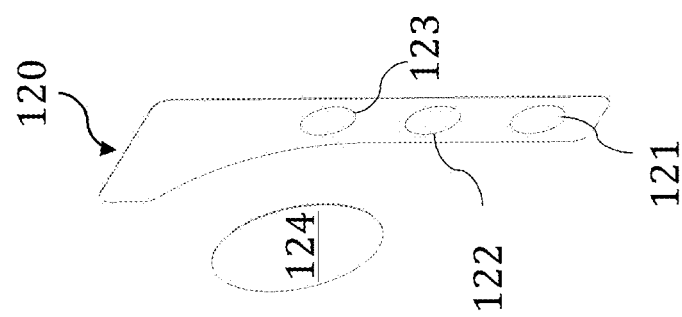
Figure 7:
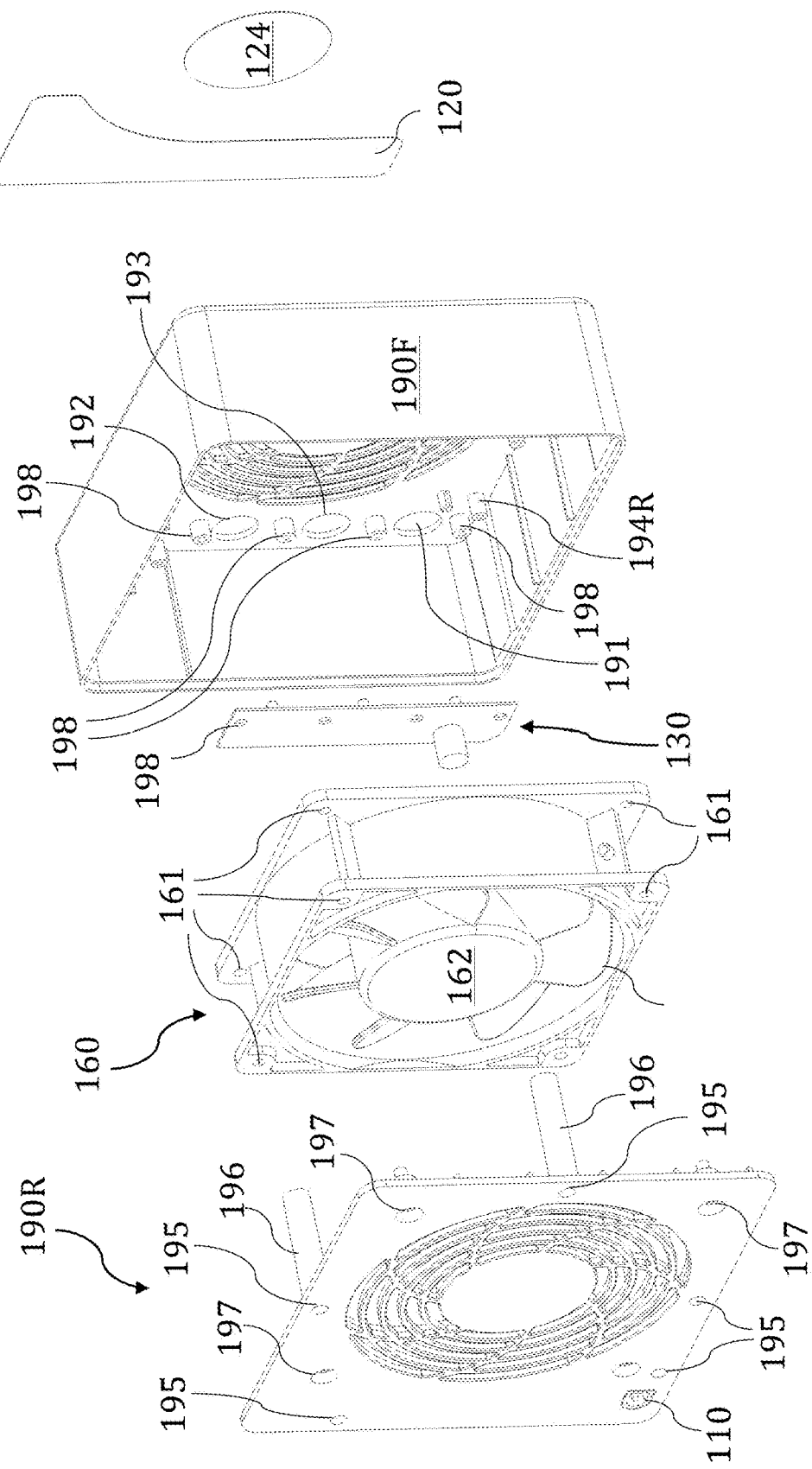
FIG. 7 is an exploded, rear perspective view of the dual function, portable fan with a three-button overlay of FIG. 6.

FIGS. 6 and 7 provide exploded perspective views of portable fan 101 from the front and rear of the fan, respectively. From left to right, portable fan 101 includes three-button control panel overlay 120, hub overlay 124, front housing portion 190F, electrical control system 130, DC axial fan 160, and rear housing portion 190R.

Overlay 120 includes demarcations 121, 122 and 123 that correspond to the positions of tactile switches 131, 132 and 133 of electrical control system 130. Electrical control system 130 is secured to the interior of front housing portion 190F in a position that allow tactile switches 131, 132 and 133 to protrude through openings 191, 192 and 193 of front housing portion 190F. Electrical control system 130 is secured to housing portion 190F through four opening 135. Demarcations 121, 122 and 123 are associated with a textual notation of fan function such as "on/off", "fan speed" or "oscillation mode"—thereby functioning as on/off, fan speed selection or oscillation mode pushbuttons that can be depressed by the user to turn the fan or oscillation mode on or off, as well as to select one of four fan speed. Thus, the electrical control system of portable fan 101 provides an on/off feature, a speed control feature and an oscillation mode selection feature that are presented to the user as three pushbuttons 121, 122 and 123 on the three-button control panel 120.

Fan 160 is a 3200 RPM, 12V, 1 Amp DC axial fan secured to the rear housing portion 190R through opening 161 on DC axial fan 160 via boss 194F and 194R on front and rear housing portion 190F and 190R. Threaded post 196 allows rear housing portion 190R to be secured to front housing portion 190F using screws at opening 195 (FIGS. 5B, 6 and 7). Rear housing portion 190R includes panel mount DC power jack 110.

To assemble portable fan 101, power jack 110 is secured to the interior side of rear housing portion 190R with screws, and similarly, electrical control system 130 is secured on the interior side of front housing portion 190F with screws. DC axial fan 160 (with motor) is secured to the fan housing through boss 194R molded at four positions on the interior side of rear housing portion 190R and boss 194F molded at four similar positions on the interior side of front housing portion 190F. The red (+) and black (−) lead wires (not shown) from power jack 110 are connected to electrical control system 130 so as to provide 12 volt DC power to electrical control system 130. The red (+) and black (−) lead wires (not shown) from axial fan 160 are also connected to electrical control system 130 so as to provide 12 volt DC power to the motor of axial fan 160. Electrical control system 130 includes a micro-controller that drives the motor of axial fan 160 and fan speeds using pulse width modulation (PWM). Electrical control system 130 includes four blue LED lights (not shown) to illuminate the On/Off, Fans Speed, and Oscillate Mode pushbuttons, three tact switches 131, 132 and 133 for each of the pushbutton control of the fan. Additional features of are further discussed below. Front and rear housing portion 190F and 190R are brought together and secured using five screws at opening 195 in rear housing portion 190R through post 196. Three-button control panel overlay 120 and logo overlay 124 can be placed on front housing portion 190F at selected locations.

The electrical control system 130 includes a fan controller, in particular, a micro-controller based, four-speed fan controller that operates from a 12 volt, 1 ampere wall adapter power supply. The controller provides DC voltages of approximately 6, 8, 10 and 12 volts to the fan as a means of controlling fan speed. In addition, the controller provides an oscillate mode that continuously ramps fan speed up and then down after pausing at maximum speed (e.g. a preselected speed) and a minimum speed (e.g. the lowest speed) to simulate the sound of a standard oscillating fan. The operator controls for electrical control system 130 consist of three momentary pushbuttons for Power On/Off, Fan Speed, and Oscillate Mode selection. When powered on, the pushbuttons are backlit with blue LED's that are illuminated brightly after actuation of any switch for 5 seconds. After the 5 seconds the LED's dim to their normal standby intensity.

Figure 8:
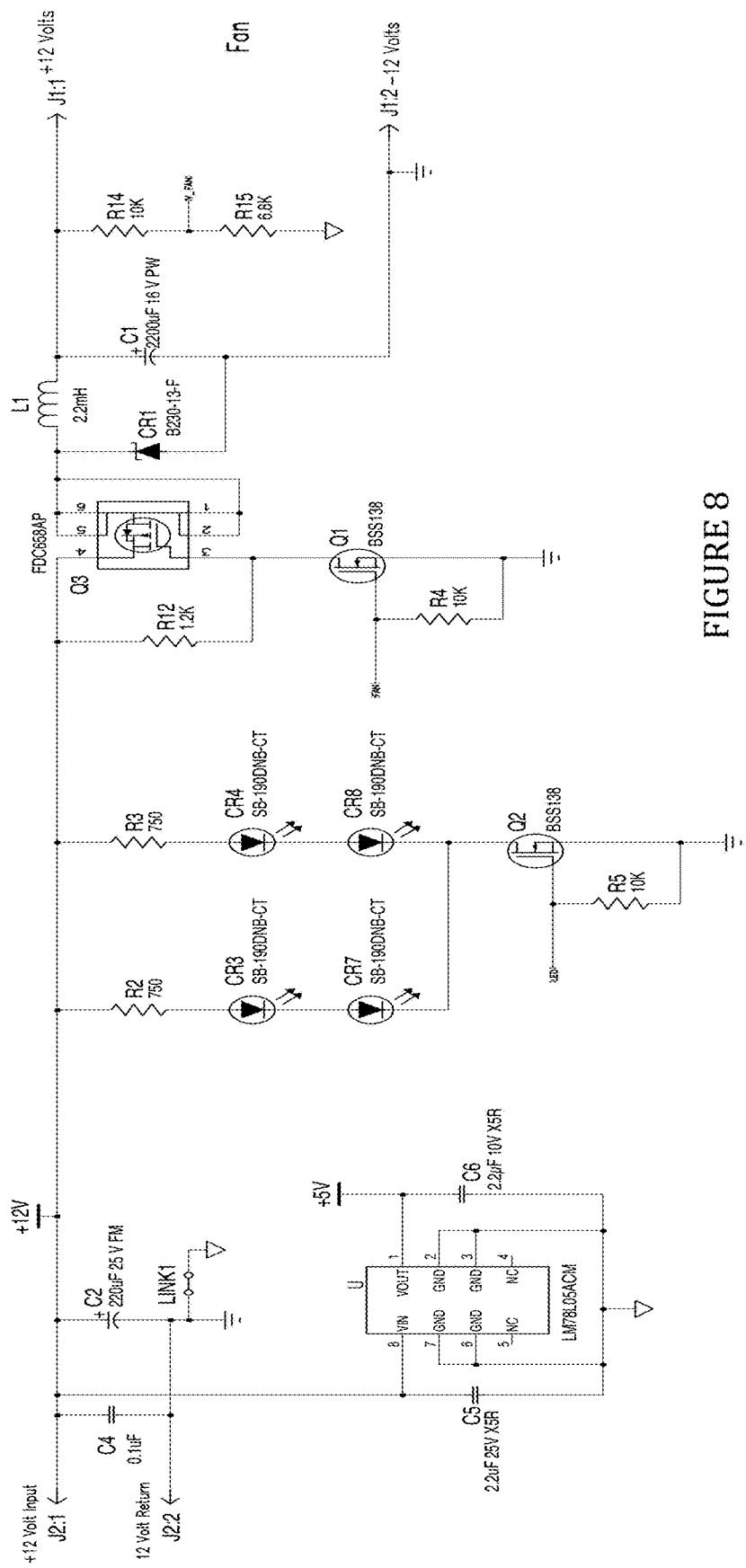
FIGS. 8-9 are circuit diagrams for electrical control system 130.
Figure 9:
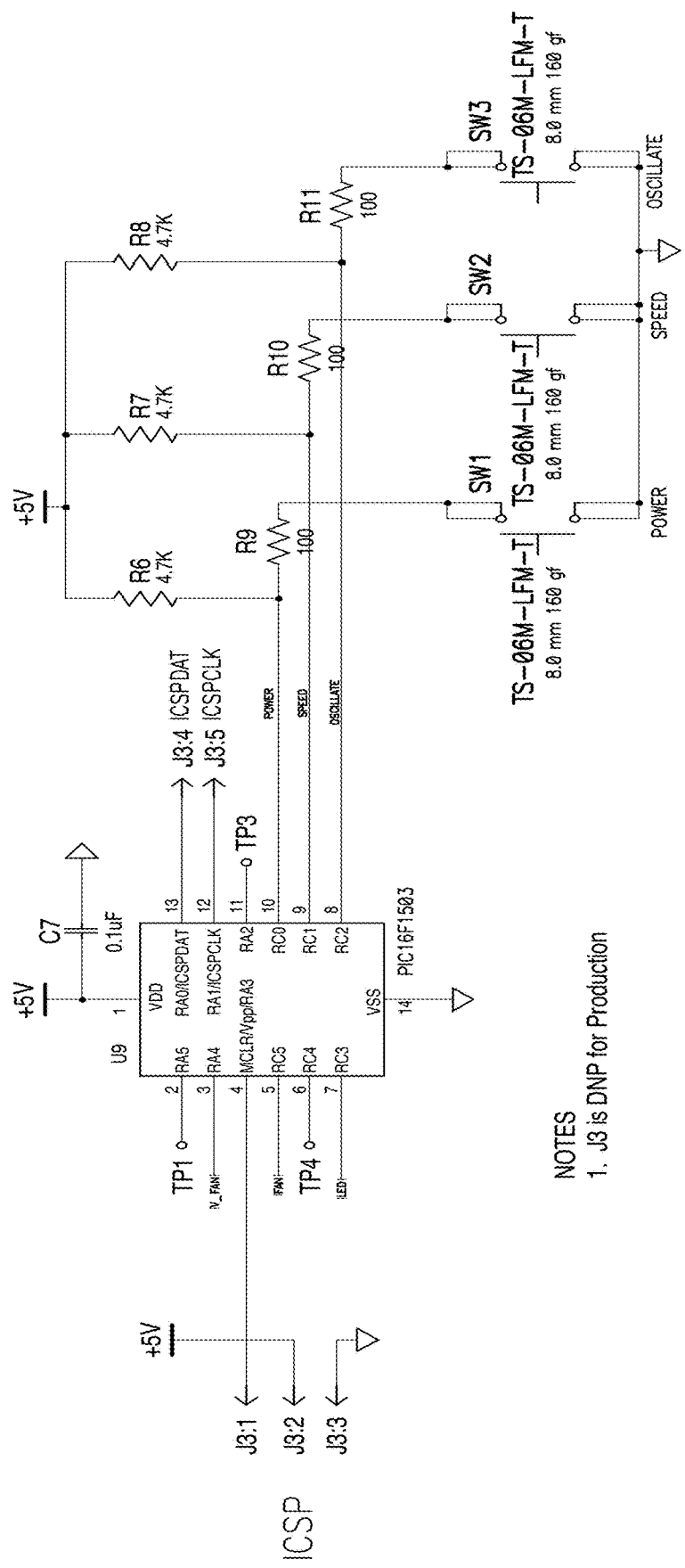

The circuitry for electrical control system 130 is illustrated in FIGS. 8 and 9, and its operation is as follows. Input power provided by the wall adapter is applied to the fan controller through connector J2 with pin 1 being +12 Volts DC and pin 2 being the 12 Volt return. This voltage input is filtered by capacitors C4, C2 and C5. The +12 volts DC is then regulated down to +5 volts DC via voltage regulator U1 to power the micro-controller U9 and its associated circuitry.

The U9 micro-controller monitors the actuation of the user interface switches SW1, SW2 and SW3, controls the on/off and dimming of the LED's, and provides a variable pulse width duty cycle square wave (FAN) to adjust the operating voltage of the fan though a buck regulator described below. The fan voltage developed by the buck regulator is monitored by the analog to digital converter inside the micro-controller on the pin labelled V_FAN. This fan voltage feedback signal is used by the micro-controller to vary the duty cycle of the FAN signal, which in turn changes the fan voltage.

The LED driver includes the LED's labeled CR3, CR4, CR7, and CR8, which are controlled via the signal LED. Resistors R2 and R3 limit the current through the LED's from the 12-volt DC supply. When the FAN signal is set to a logic High by the micro-controller U9, the LED driver MOSFET Q2 is turned on allowing current to flow through the LED's. To further dim the LED's, the micro-controller modulates Q2 on and off at a low duty cycle to give the visual effect of dimming.

The three interface switches for Power On/Off, Fan Speed, and Oscillate Mode selection are labeled SW1, SW2 and SW3 respectively. The switch inputs to the micro-controller are normally logic High due to the pull-up resistors R6, R7 and R8 being tied to the +5 V DC power bus. When the switches are actuated, the pull-up resistors are pulled to ground through the switch and the associated 100 ohm resistor, thus creating a logic Low on the input to the micro-controller that is then recognized as the user selecting a function. For the SPEED switch SW2, speed is increased for every incremental actuation until maximum speed is obtained. If actuated again, the speed goes back to the lowest setting. Thus, by actuating the switch, the fan continuously cycles through the various speeds. The fan voltage is developed by the buck regulator, which includes components R12, Q3, Q1, R4, CR1, L1, C1, R14 and R15. The micro-controller produces a 5 KHz pulse train on the FAN signal with a positive duty cycle that varies from 50% to 100%. A logic High on the FAN signal causes Q1 to turn on Q3 which then applies the 12 volt DC bus to the input of inductor L1. This in turn causes current to linearly increase through L1. When the FAN signal is switched Low, Q3 is turned off and then as the magnetic field of the inductor collapses it pushes current into C1 developing a voltage for the fan motor. This process occurs approximately 5,000 times a second creating a DC voltage on C1 to drive the fan. This fan voltage is proportional to the duty cycle of the FAN signal. Thus at 50% duty cycle the fan voltage is 50% of the 12 volt DC bus or 6 volts. The fan voltage is divided down by resistors R14 and R15 to a safe value for the micro-controller to measure. The duty cycle is adjusted as needed to keep the fan voltage at the required value for a given fan speed.

The oscillation mode of operation is achieved by the micro-controller slowly and continuously changing the duty cycle from 50% to 100% and then back down to 50% with delays at the minimum and maximum duty cycles. This causes the fan voltage (and thus the fan speed) to be increased from 6 volts to 12 volts over several seconds, remain at 12 volts for several seconds, and then decrease back to 6 volts over several seconds. After several seconds at 6 volts, the cycle repeats. This change in fan speed with delays at minimum and maximum speeds gives the audible perception of a standard oscillating fan. Header J3 is used to program the micro-controller with operational firmware at the factory.

Other Embodiments of the Invention

While the invention has been described in conjunction with the detailed description, the foregoing description is intended to illustrate and not limit the scope of the invention, which is defined by the scope of the claims. Other aspects, advantages, modifications and variations are within the scope of the following claims. Under no circumstances may the patent application be interpreted to be limited to the specific examples or embodiments or methods specifically disclosed herein.

The terms and expressions employed herein are used as terms of description and not of limitation. There is no intent in the use of such terms and expressions to exclude any equivalent of the features shown and described or portions thereof.

The invention has been described broadly and generically herein. Each of the narrower species and subgeneric groupings falling within the generic disclosure also form part of the invention. As used herein and in the appended claims, the singular forms "a," "an," and "the" include plural reference unless the context clearly dictates otherwise.

What is claimed is:

1. The A portable DC cooling fan, comprising:
   (a) a non-oscillating DC axial fan electrically connected to an electrical control circuitry to enable the electrical control circuitry to control operation of the fan, the electrical control circuitry being electrically connected to a DC power jack and comprising at least one user interface switch through which a user can control operation of the DC axial fan; and
   (b) a housing within which the non-oscillating DC axial fan is secured comprising an opening through which the DC power jack is mounted, an opening for accommodating the user interface switch to enable access to the switch from the exterior of the housing, and a plurality of regularly-spaced openings aligned with the blades of the axial fan to enable air intake and egress through the housing;
   wherein the electrical control circuitry comprises three tactile user interface switches, a fan micro-controller for monitoring the actuation of the tactile switches, and a buck regulator through which the fan micro-controller adjusts the DC voltage being provided to the fan;
   wherein each of the tactile switches is accessible from the exterior of the housing thereby enabling the user to actuate the switch from the exterior of the housing; and each of the tactile switches is electrically connected to the fan micro-controller, which is electrically connected to a buck regulator configured to provide operating voltage to the fan to allow the user to control fan operation by actuating one or more tactile switches;
   wherein: (a) actuation of a first tactile switch causes the micro-controller to turn the fan on or off; (b) actuation of a second tactile switch configured for fan speed selection causes the micro-controller to alter the speed of the DC axial fan; and (c) actuation of a third tactile switch configured for oscillation mode selection causes the micro-controller to turn on or off fan speed oscillation.

2. The portable DC cooling fan of claim 1, wherein actuation of the tactile switch for fan speed selection causes a change in the DC voltage being provided to the fan motor thereby enabling the user to affect fan speed.

3. The portable DC cooling fan of claim 1, wherein each actuation of the tactile switch for fan speed selection causes fan speed to increase to the next higher speed increment, and actuation of the tactile switch for fan speed selection when the fan is operating at the highest possible speed causes fan speed to return to the lowest speed.

4. The portable DC cooling fan of claim 1, wherein the buck regulator is configured to provide an operating voltage of at least one of 6 volts, 8 volts, 10 volts, or 12 volts, at a given time, to the motor of the DC axial fan.

5. The portable DC cooling fan of claim 1 further comprising: (a) a membrane overlay with demarcation indicating the position of at least one of the tactile switches, (b) notation indicating a function of at least one of the tactile switches when actuated, (c) a LED light source for illuminating at least one of the tactile switches, the LED being under the control of the fan micro-controller, or (d) any combination thereof.

6. The portable DC cooling fan of claim 1, wherein the fan is powered using a current of 1 ampere or less.

7. The portable DC cooling fan of claim 1, wherein the electrical control circuitry operates from a 12 volt, 1 ampere AC/DC adapter power supply.

8. The portable device of claim 1, wherein the DC axial fan has an air output at 12 to 200 cubic feet per minute.

9. The portable DC cooling fan of claim 1, wherein the buck regulator is configured to provide a first operating voltage for a first phase of the fan, a second operating voltage for a second phase of the fan, a third operating voltage for a third phase of the fan, and a fourth operating voltage for a fourth phase of the fan.

10. A portable DC cooling fan comprising:
    (a) a DC axial fan electrically connected to an electrical control system to enable the electrical control system to control operation of the fan, the electrical control system being electrically connected to a DC power jack and comprising: (i) three tactile user interface switches through which a user can control operation of the DC axial fan, (ii) a fan micro-controller to which the three tactile switches are electrically connected for monitoring the actuation of the tactile switches, and (iii) a buck regulator through which the fan micro-controller adjusts the DC voltage provided to the fan; and
    (b) a housing within which the DC axial fan is secured comprising (i) an opening through which the DC power jack is mounted, (ii) an opening for accommodating each of the user interface switches to enable access to the switch from the exterior of the housing, and (iii) a plurality of regularly-spaced openings substantially aligned with the blades of the axial fan to enable efficient air intake and egress through the housing,
    wherein actuation of a first tactile switch causes the micro-controller to turn the fan on or off, actuation of a second tactile switch configured for fan speed selection causes the micro-controller to alter the speed of the DC axial fan, and actuation of a third tactile switch configured for oscillation mode selection causes the micro-controller to turn on or off fan speed oscillation;

wherein selection of fan speed oscillation mode causes the portable DC cooling fan to continuously cycle through four fan operation phases: a first phase during which the fan is maintained at a pre-selected speed for a first period of time, a second phase during which fan speed decreases from the pre-selected speed to the lowest setting over a second period of time, a third phase during which fan speed is maintained at the lowest fan speed for a third period of time, and a fourth phase during which fan speed increases from the lowest fan speed to the pre-selected speed over a fourth period of time.

11. The portable DC cooling fan of claim 10, wherein the first and third periods are about 2 to about 3 seconds.

12. The portable DC cooling fan of claim 11, wherein the second and fourth periods are about 5 to about 6 seconds.

13. The portable DC cooling fan of claim 10, wherein the first and third time periods have a shorter duration than the second and fourth time periods.

14. The portable cooling fan of claim 10, wherein the buck regulator is configured to provide an operating voltage of at least one of 6 volts, 8 volts, 10 volts, or 12 volts, at a given time, to the motor of the DC axial fan.

15. The portable DC cooling fan of claim 10, wherein the fan is powered using a current of 1 ampere or less.

16. The portable device of claim 10, wherein the DC axial fan has an air output at 12 to 200 cubic feet per minute.

17. A portable cooling fan comprising:
(a) a non-oscillating fan;
(b) an electrical control circuitry electrically connected to the fan to control operation of the fan;
(c) at least one control switch through which the electrical control circuitry receives input to control operation of the fan; and
(d) a housing securing the fan and supporting the control switch to enable access to the switch from the exterior of the housing, the housing having a plurality of openings air intake and egress through the housing for fan operation;
wherein the electrical control circuitry is configured to enable a user to select fan speed oscillation mode to cause the fan to continuously cycle through at least two constant fan speeds and at least two periods of fan speed changes, wherein the at least two constant fan speeds are different and simulate sounds of an oscillating fan at two extreme positions of oscillation, respectively, and wherein the at least two periods of fan speed changes simulate sounds of the oscillating fan intermediate the two extreme positions of oscillation.

18. The portable cooling fan of claim 17, wherein the fan is powered using a current of 1 ampere or less.

19. The portable DC cooling fan of claim 17, further comprising: (a) a membrane overlay with demarcation indicating the position of at least one of the tactile switches, (b) notation indicating a function of at least one of the tactile switches, (c) an LED light source for illuminating at least one of the tactile switches, the LED being under the control of the fan micro-controller, or (d) any combination thereof.

20. The portable device of claim 17, wherein the DC axial fan has an air output at 12 to 200 cubic feet per minute.

* * * * *